United States Patent [19]
Okonogi et al.

[11] Patent Number: 4,970,305
[45] Date of Patent: Nov. 13, 1990

[54] CRYSTALLINE DIHYDROCHLORIDE OF CEPHALOSPORIN DERIVATIVE AND A METHOD FOR PREPARATION THEREOF

[75] Inventors: Tsuneo Okonogi; Yasushi Murai; Masahiro Onodera; Toshio Nishizuka; Yasuhiko Arai Seiji Shibahara; Shigeharu Inouye, all of Yokohama, Japan

[73] Assignee: Meiji Seika Kaisha, Ltd., Tokyo, Japan

[21] Appl. No.: 413,915

[22] Filed: Sep. 28, 1989

[30] Foreign Application Priority Data

Oct. 8, 1988 [JP] Japan ................... 63-254340

[51] Int. Cl.$^5$ .................. C07D 501/36; A61K 31/545
[52] U.S. Cl. ................................................ 540/225
[58] Field of Search ................... 540/222, 225, 227; 514/206

[56] References Cited

U.S. PATENT DOCUMENTS 4,810,702  3/1989  Shibahara et al. ................ 540/226

Primary Examiner—Nicholas S. Rizzo
Attorney, Agent, or Firm—Jordan and Hamburg

[57] ABSTRACT

The crystalline dihydrochloride of a specific cephalosporin derivative is stable to heat and retains its antibacterial activity even after storage over long periods at high temperature. The crystalline dihydrochloride can be obtained by removing protective groups from the cephalosporin derivative wherein the amino group and carboxy groups are protected and then crystallizing the cephalosporin derivative from a hydrochloric acid aqueous solution. The crystalline dihydrochloride is useful for pharmaceutical preparations.

2 Claims, No Drawings

CRYSTALLINE DIHYDROCHLORIDE OF CEPHALOSPORIN DERIVATIVE AND A METHOD FOR PREPARATION THEREOF

BACKGROUND OF THE INVENTION

1. Field of the Invention

The present invention relates to crystalline dihydrochloride of (6R,7R)-7-[(Z)-2-(2-aminothiazol-4-yl)-2-((1S)-1-carboxyethoxyimino)acetamido]-3-[(1-ethylpyridinium-4-yl)thiomethyl]ceph-3-em-4-carboxylate which is stable to heat and useful for pharmaceutical preparation and medical application, and a method for preparation thereof.

2. Prior Art (6R,7R)-7-[(z)-2-(2-Aminothiazol-4-yl) 2-((1S)-1-carboxyethoxyimino)acetamido]-3-[(1-ethylpyridinium-4-yl)thiomethyl]ceph-3-em-4-carboxylate is disclosed in Japanese Patent KOKAI No. 63-154622 as an amorphous sodium salt. This compound is an excellent compound having an antibacterial spectrum over a wide range including gram-positive bacteria to gram-negative bacteria.

As is described above, the amorphous sodium salt of the cephalosporin derivative described above is an extremely excellent compound which is non-toxic and has an antibacterial spectrum over a wide range. However, due to lack of thermal stability, this compound is not satisfactory for medical preparations and medical application.

SUMMARY OF THE INVENTION

An object of the present invention is to improve the thermal stability of this cephalosporin derivative and provide its crystalline salt which can be easily be used for medical preparations and can readily be applied to medical use.

The present inventors have made extensive investigations on (6R,7R)-7-[(Z)-2-(2-aminothiazol-4-yl)-2-((1S)-1-carboxyethoxyimino)acetamido]-3-[(1-ethylpyridinium-4-yl)thiomethyl]ceph-3-em-4-carboxylate shown by formula (1):

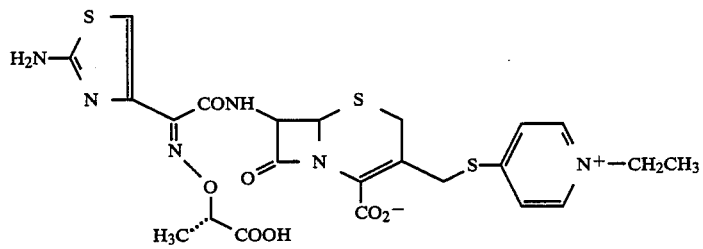

(1)

especially with respect to its heat stability. Paying attention to the fact that the purified product of this compound is obtained in the form of an amorphous solid, the amorphous solid has been converted into a crystalline dihydrochloride. As a result, it has been found that little activity is lost even during storage over long periods of time at high temperature and the present invention has thus been accomplished.

The present invention relates to the crystalline dihydrochloride of (6R,7R)-7-[(Z)-2-(2-aminothiazol-4-yl)-2-((1S)-1-carboxyethoxyimino)acetamido]3-[(1-ethyl-pyridinium-4-yl)thiomethyl]ceph-3-em-4-carboxylate as well as to a method for preparing the crystalline dihydrochloride of (6R,7R)-7-[(Z)-2-(2-aminothiazol-4yl)-2-((1S)-1-carboxyethoxyimino)acetamido]-3-[(1ethyl-pyridinium-4-yl)thiomethyl]ceph-3-em-4-carboxylate which comprises removing protective groups from the cephalosporin derivative of formula (1) wherein the amino group and carboxyl group are protected and then crystallizing the cephalosporin derivative from a hydrochloric acid aqueous solution.

DESCRIPTION OF THE PREFERRED EMBODIMENTS

To prepare the aforesaid crystalline dihydrochloride of the cephalosporin derivative of the present invention, the cephalosporin derivative shown by formula (1) wherein the amino group at the 2-position of the thiazole ring, the carboxy group at the 1-position of the ethoxyimino group and the carboxy group at the 4-position of the cephem ring are protected with protective groups ordinarily used for synthesis of cephalosporin compounds such as trityl group, methoxybenzyl group, diphenylmethyl group, etc., and then are subjected to reactions for removing the protective groups such as acid decomposition with an acid such hydrochloric acid, sulfuric acid, hydrobromic acid, etc. (preferably hydrochloric acid) using formic acid as a solvent or by heating in formic acid at about 30° to 50° C. without adding any acid, whereby the protective groups are split off.

The compound from which the protective groups are thus split off is isolated in the form of an amorphous salt or zwitter ions of the cephalosporin derivative of formula (1). The crystalline dihydrochloride of the cephalosporin derivative of the present invention shown by formula (1) may be obtained by dissolving the isolated compound in a hydrochloric acid aqueous solution and crystallizing from the solution under cooling; or, alternatively, by extracting the reaction mixture with a water-immiscible organic solvent and water, without isolating these amorphous solids, separating the aqueous layer and adding hydrochloric acid and a water-miscible organic solvent to the aqueous layer to cause crystallization.

When the acid deprotection is performed in the reaction of removing the protective groups upon isolation of the amorphous salt, an organic solvent such as acetone, methyl ethyl ketone, methyl isobutyl ketone, ethanol, n-propanol, isopropanol, etc., preferably acetone, is added to the system to give the precipitates which are isolated. Thus, the amorphous salt of the cephalosporin derivative shown by formula (1) can be obtained. By this treatment, triphenylmethanol, diphenylmethanol, p-methoxybenzyl alcohol, etc. which are released upon the removal of the protective groups are dissolved in the organic solvent and eliminated.

Crystals are precipitated from a hydrochloric acid aqueous solution of the amorphous salt of the thus obtained cephalosporin derivative shown by formula (1), preferably in an aqueous solution containing 6 or more molar equivalents of hydrochloric acid at 0° to 10° C. over about 10 hours or longer, by adding seed crystals to the aqueous solution. Then, the crystalline dihydrochloride of the cephalosporin derivative shown by formula (1) can be obtained.

To isolate the amorphous zwitter ion compound, the reaction mixture at the time when the reaction of removing the protective groups is completed is added to isopropyl alcohol, etc. at 0° to 10° C. The pH is adjusted to 3.7 to 4.2 with an organic base such as ammonia, triethylamine, pyridine, etc., preferably conc. ammonia water, whereby precipitates are formed to isolate the amorphous zwitter ions of the cephalosporin derivative shown by formula (1). The amorphous zwitter ion compound may also be readily obtained by adjusting the pH of the amorphous sodium salt disclosed in Japanese Patent KOKAI No. 63-154622 to 4.0 with hydrochloric acid in an alcohol.

The amorphous zwitter ion compound is dissolved in water using hydrochloric acid and conc. hydrochloric acid is added to the aqueous solution at a low temperature. In this case, the amorphous zwitter ion compound is dissolved in less than a 10-fold amount of water using about 3 molar equivalents of hydrochloric acid and at least 5 molar equivalents of conc. hydrochloric acid is used at 0° to 10° C. Seed crystals are added to the solution and crystals are precipitated over 10 hours or longer to give the crystalline dihydrochloride of the cephalosporin derivative shown by formula (1).

To obtain the crystalline dihydrochloride from the reaction mixture in the removal of the protective groups with formic acid and hydrochloric acid without isolating the amorphous solid, the aqueous layer is separated from the reaction solution at the time when the reaction of removing the protective groups is completed followed by washing with a water-immiscible organic solvent such as diethyl ether, diisopropyl ether, ethyl acetate, etc., preferably diisopropyl ether. Then, water, a water-miscible organic solvent such as acetone, etc. and hydrochloric acid are added to the system. Water, acetone and hydrochloric acid are advantageously added in amounts ranging from 4 to 6 times, from 10 to 20 times and 0 to 5 molar equivalents to dihydrochloride in the aqueous solution, respectively.

Crystals are precipitated from the solution at 0° to 10° C. over 10 hours or more by adding seed crystals to the solution.

The thus precipitated crystals are isolated in a conventional manner, for example, by filtration in vacuum. The crystals are then washed with an organic solvent such as acetone, methyl ethyl ketone, methanol, ethanol, n-propanol, isopropanol, etc., singly or in combination, preferably using a solvent mixture of acetone and ethanol. Thereafter the crystals are dried at 30° to 60° C. under reduced pressure to give the crystalline dihydrochloride of the cephalosporin derivative shown by formula (1).

In the method described above, the procedure for precipitating the crystalline dihydrochloride from the reaction product after removing the protective groups without isolating the amorphous solid is industrially suitable since the isolation step can be omitted.

The thus obtained crystalline dihydrochloride of the cephalosporin derivative shown by formula (1) is needles of extremely high purity and contains at least 2 molecules of hydrochloric acid per 1 molecule of cephalosporin and contains less than 4.0 % (by weight) of water.

The present substance can be stored at room temperature over long periods of time or at 60° C. or higher for a week. In this case, the antibacterial activity of the cephalosporin derivative shown by formula (1) is hardly lost.

Next, the present invention is described in more detail by referring to the examples but is not deemed to be limited thereto.

EXAMPLE 1

In 50.8 ml of 88 % formic acid was dissolved 25.4 g of p-methoxybenzyl (6R,7R)-7-[(Z) 2-(2-ritylaminothiazol-4-yl)-2-((1S)-1-diphenylmethoxycarbonylethoxyimino)acetamido]-3-[(1-ethylpyridinium-4-yl)thiomethyl]ceph-3-em-4-carboxylate chloride, and 25.4 ml of anisole was added to the solution. After cooling to 15° to 20° C., 12.7 ml of 36% hydrochloric acid was added to the mixture. After stirring at 20° to 22° C. for 4 hours, the aqueous layer was separated and washed with isopropyl ether.

To 39 ml of the aqueous layer were added 17 ml of water and 187 ml of acetone. After cooling to 0° to 5° C., seed crystals were added and stirring was continued overnight to precipitate crystals. The crystals were filtered under reduced pressure and washed with 21 ml of a solvent mixture of acetone and ethanol (4:1). Drying at 40° C. overnight under reduced pressure gave 10.2 g (71%) of the crystalline dihydrochloride of (6R,7R)-7-[(Z)-2-(2-aminothiazol-4-yl)-2-((1S)-1-carboxyethoxyimino)acetamido]-3-[(1-ethylpyridinium-4-yl)thiomethyl]ceph-3-em-4-carboxylate.

NMR (D$_2$O) &: 1.57 (d, J 6.92 Hz), 1.57 (t, J 7.44 Hz), 3.58 and 3.79 (ABq, J =17.9 Hz), 4.39 and 4.43 (ABq, J =13.3 Hz), 4.47 (q, J=7.44 Hz), 4.98 (q, J =6.92 Hz), 5.25 (q, J= 4.62 Hz), 5.82 (d, J =4.62 Hz), 7.23 (s), 7.83 and 8.51 (ABq, J =7.18 Hz).

IR (KBr) $\nu$ max: 1770, 1709, 1660, 1625 cm$^{-1}$.

UV (H$_2$O) $\lambda$ max: 304, 259, 231 nm.

Melting point: 180°-183° C. (decomp.).

$[\alpha]_n$: — 34.3 (c 1.0, H$_2$O).

Karl Fischer's analysis of water content: 3.46%.

EXAMPLE 2

In 50.8 ml of 88 % formic acid was dissolved 25.4 g of p-methoxybenzyl (6R,7R)-7-[(Z)-2-(2-tritylaminothiazol-4-yl)-2-((1S)- 1-diphenylmethoxycarbonylethoxyimino)acetamido]-3-[(1-ethylpyridinium-4-yl)thiomethyl]ceph-3-em-4-carboxylate chloride, and 25.4 ml of anisole was added to the solution. After cooling to 15° to 20° C., 12.7 ml of 36% hydrochloric acid was added to the mixture. After stirring at 20° to 22° C. for 4 hours, the reaction mixture was added to 1.02 liters of a solvent mixture of acetone and the isopropyl ether (4:1) to form precipitates. The precipitates were filtered and dried to give 11.2 g of the dihydrochloride as amorphous solid.

The dihydrochloride was dissolved in 80 ml of water, and 8.42 ml of 36 % hydrochloric acid was added to the solution. After stirring at 0° to 5° C., seed crystals were added and stirring was continued overnight to precipitate crystals. The crystals were filtered under reduced pressure and washed with 20 ml of a solvent mixture of acetone and ethanol (4:1). Drying at 40° C. overnight under reduced pressure gave 9.63 g (66% of the same crystalline dihydrochloride as the product of Example 1.

EXAMPLE 3

In 112 ml of 88 % formic acid was dissolved 56.2 g of p-methoxybenzyl (6R, 7R)-7[(Z)-2-(2-tritylaminothiazol-4-yl)-2-((1S)- 1-diphenylmethoxycarbonylethoxyimino)acetamido]-3-[(1-ethylpyridinium-4-yl)thiomethyl]ceph-3-em-4-carboxylate chloride, and 56 ml of anisole was added to the solution. After cooling to 15° to 20° C., 28.1 ml of 36 % hydrochloric acid was added to the mixture. After stirring at 20° to 22° C. for 4 hours, the reaction mixture was added to 1.70 liter of isopropanol cooled to 10° C. or below. The pH was adjusted to 3.7 to 4.0 with 25% ammonia water to form precipitates. The precipitates were filtered and dried to give 42.2 g (purity, 50 %) of zwitter ions containing ammonium chloride.

The zwitter ions were dissolved in 102 ml of water using 4.65 ml of 36 % hydrochloric acid, and 7.75 ml of 36% hydrochloric acid was added to the solution at 10° C. or below. After cooling to 0° to 5° C., seed crystals were added and stirring was continued overnight to precipitate crystals. The crystals were filtered under reduced pressure and washed with 20 ml of a solvent mixture of acetone and ethanol (4:1). Drying at 40° C. overnight under reduced pressure gave 20.3 g (63 %) of the same crystalline dihydrochloride as the product of Example 1.

The present invention provides the crystalline dihydrochloride of (6R,7R)-7-[(Z)-2-(2-aminothiazol-4-yl)-2-((1S)-1-carboxyethoxyimino)acetamido]-3-[(1-ethylpyridinium-4-yl)thiomethyl]ceph-3-em-4-carboxylate which is improved in heat stability and a process for preparing the crystalline dihydrochloride. The present invention is extremely useful both in making pharmaceutical preparations of the cephalosporin derivative described above and applying the same to the medical field.

While the invention has been described in detail and with reference to specific embodiments thereof, it is apparent to one skilled in the art that various changes and modifications can be made therein without departing from the spirit and scope of the present invention.

What is claimed is:

1. Crystalline dihydrochloride of (6R,7R)-7-[(Z)-2-(2-aminothiazol-4-yl)-2-((1S)-1-carboxyethoxyimino)acetamido]-3-[(1-ethylpyridinium-4-yl)thiomethyl]ceph-3-em-4-carboxylate.

2. A method for preparation of (6R,7R)-7-[(Z)-2-(2-aminothiazol-4-yl)-2-((1S)-1-carboxyethoxyimino)acetamido]-3-[(1-ethylpyridinium-4-yl)thiomethyl]ceph-3-em-4-carboxylate which comprises removing protective groups from (6R,7R)-7-[(Z)-2-(2-aminothiazol-4-yl)-2-((1S)-1-carboxyethoxyimino)acetamido]-3-[(1-ethylpyridinium-4-yl)thiomethyl]ceph-3-em-4-carboxylic acid wherein the amino group and carboxyl groups are protected and then crystallizing the carboxylic acid from a hydrochloric acid aqueous solution.

* * * * *